(12) United States Patent
Naylor et al.

(10) Patent No.: US 9,226,900 B2
(45) Date of Patent: Jan. 5, 2016

(54) PROCESS FOR PREPARING MICROPARTICLES

(75) Inventors: Andrew Naylor, Nottingham (GB); Andrew Lester Lewis, Nottingham (GB); Lisbeth Illum, Nottingham (GB)

(73) Assignee: Critical Pharmaceuticals Limited, Nottingham (GB)

( * ) Notice: Subject to any disclaimer, the term of this patent is extended or adjusted under 35 U.S.C. 154(b) by 668 days.

(21) Appl. No.: 13/003,506

(22) PCT Filed: Jul. 10, 2009

(86) PCT No.: PCT/GB2009/001711
§ 371 (c)(1),
(2), (4) Date: Mar. 10, 2011

(87) PCT Pub. No.: WO2010/004287
PCT Pub. Date: Jan. 14, 2010

(65) Prior Publication Data
US 2011/0172141 A1    Jul. 14, 2011

(30) Foreign Application Priority Data
Jul. 11, 2008  (GB) .................................... 0812742.5

(51) Int. Cl.
A61K 9/00       (2006.01)
A61K 38/00      (2006.01)
A61K 9/16       (2006.01)

(52) U.S. Cl.
CPC ............. *A61K 9/1694* (2013.01); *A61K 9/1647* (2013.01)

(58) Field of Classification Search
CPC .......................... A61K 9/1694; A61K 9/1647
See application file for complete search history.

(56) References Cited

U.S. PATENT DOCUMENTS

| | | | |
|---|---|---|---|
| 4,548,990 A | 10/1985 | Mueller et al. | 525/123 |
| 4,582,731 A | 4/1986 | Smith | 427/427 |
| 4,598,006 A | 7/1986 | Sand | 514/291 |
| 4,713,243 A | 12/1987 | Schiraldi | 424/676 |
| 4,734,227 A | 3/1988 | Smith | 264/13 |
| 4,734,451 A | 3/1988 | Smith | 524/493 |
| 4,820,752 A | 4/1989 | Berens et al. | 523/340 |
| 5,043,280 A | 8/1991 | Fischer et al. | 435/235.1 |
| 5,158,986 A | 10/1992 | Cha et al. | 521/82 |
| 5,290,827 A | 3/1994 | Shine | 523/340 |
| 5,340,614 A | 8/1994 | Perman et al. | 427/2.24 |
| 5,399,597 A | 3/1995 | Mandel et al. | 523/342 |
| 5,508,060 A | 4/1996 | Perman et al. | 427/2.14 |
| 5,548,004 A | 8/1996 | Mandel et al. | 523/342 |
| 5,624,747 A * | 4/1997 | Sarkar et al. | 428/32.14 |
| 5,679,737 A | 10/1997 | DeSimone et al. | 524/529 |
| 5,698,163 A | 12/1997 | Mandel | 422/105 |
| 5,744,163 A | 4/1998 | Kim et al. | 424/489 |
| 5,766,367 A | 6/1998 | Smith et al. | 134/2 |
| 5,766,637 A | 6/1998 | Shine et al. | 424/497 |
| 5,776,637 A | 7/1998 | Kashio et al. | 429/217 |
| 5,866,053 A | 2/1999 | Park et al. | 264/50 |
| 6,051,174 A | 4/2000 | Park et al. | 264/50 |
| 6,056,791 A | 5/2000 | Weidner et al. | 23/295 R |
| 6,087,003 A | 7/2000 | Benoit et al. | 428/403 |
| 6,183,783 B1 | 2/2001 | Benoit et al. | 424/497 |
| 6,248,363 B1 | 6/2001 | Patel et al. | 424/497 |
| 6,403,672 B1 | 6/2002 | Randolph et al. | 522/79 |
| 6,414,050 B1 | 7/2002 | Howdle et al. | 523/105 |
| 6,521,258 B1 | 2/2003 | Mandel et al. | 424/484 |
| 6,579,532 B1 | 6/2003 | Mandel et al. | 424/423 |
| 6,620,351 B2 | 9/2003 | Gupta et al. | 264/7 |
| 6,673,286 B2 | 1/2004 | Shih et al. | 264/50 |
| 6,828,363 B2 | 12/2004 | Beuermann et al. | 524/81 |
| 6,864,301 B2 | 3/2005 | Randolph et al. | 522/74 |
| 6,913,779 B2 | 7/2005 | Colombo et al. | 427/2.24 |
| 6,931,888 B2 | 8/2005 | Shekunov et al. | 62/540 |
| 6,966,990 B2 | 11/2005 | Chattopadhyay et al. | 210/634 |
| 6,967,028 B2 | 11/2005 | Dulieu et al. | 424/501 |
| 6,986,846 B2 | 1/2006 | Shekunov et al. | 210/634 |
| 6,998,051 B2 | 2/2006 | Chattopadhyay et al. | 210/634 |

(Continued)

FOREIGN PATENT DOCUMENTS

| EP | 0 332 687 | 9/1989 |
|---|---|---|
| EP | 0 364 944 | 4/1990 |

(Continued)

OTHER PUBLICATIONS

Sessa, Phospholipid spherules (liposomes) as a model for biological membranes, Journal of Lipid Research 9:310-318, 1968.*

(Continued)

*Primary Examiner* — Julie Ha
*Assistant Examiner* — Li Ni Komatsu
(74) *Attorney, Agent, or Firm* — LeClairRyan, a Professional Corporation

(57) ABSTRACT

A process for preparing microparticles comprising a biologically active material and a polymer and having a mean particle size expressed as the volume mean diameter (VMD) of from 10 to 500 μm, wherein the biologically active material is substantially insoluble in the polymer, which process comprises: a. contacting a mixture of the biologically active material or a precursor thereof, the polymer or a precursor thereof and a processing aid with a supercritical fluid which is capable of swelling the polymer under temperature and pressure conditions necessary to maintain the fluid in a supercritical state; b. allowing the supercritical fluid to penetrate and liquefy the polymer, while maintaining the temperature and pressure conditions so that the fluid is maintained in a supercritical state; c. releasing the pressure to precipitate microparticles comprising the biologically active agent and the polymer.

10 Claims, 4 Drawing Sheets

(56) References Cited

U.S. PATENT DOCUMENTS

| | | | |
|---|---|---|---|
| 2002/0000681 A1 | 1/2002 | Gupta et al. | 264/9 |
| 2002/0130430 A1 | 9/2002 | Castor | 264/14 |
| 2003/0109421 A1 | 6/2003 | Palakodaty et al. | 264/12 |
| 2003/0161884 A1 | 8/2003 | Rosenberg et al. | 424/486 |
| 2003/0215515 A1 | 11/2003 | Truong-Le et al. | 424/489 |
| 2004/0026319 A1 | 2/2004 | Chattopadhyay et al. | 210/634 |
| 2004/0043076 A1 | 3/2004 | Dulieu et al. | 424/490 |
| 2004/0154317 A1 | 8/2004 | Shekunov et al. | 62/64 |
| 2004/0154985 A1 | 8/2004 | Shekunov et al. | 210/634 |
| 2004/0156911 A1 | 8/2004 | Chattopadhyay et al. | 424/489 |
| 2004/0200774 A1 | 10/2004 | Shekunov et al. | 210/634 |
| 2004/0247624 A1 | 12/2004 | Unger et al. | 424/400 |
| 2005/0012205 A1 | 1/2005 | Dias et al. | 257/712 |
| 2005/0082701 A1 | 4/2005 | Shekunov et al. | 264/5 |
| 2005/0178020 A1 | 8/2005 | Shekunov et al. | 34/284 |
| 2005/0192371 A1 | 9/2005 | Randolph et al. | 522/79 |
| 2006/0008531 A1 | 1/2006 | Shekunov et al. | 424/489 |
| 2006/0033224 A1 | 2/2006 | Castor | 264/13 |
| 2006/0039983 A1 | 2/2006 | Shekunov et al. | 424/489 |
| 2006/0076293 A1 | 4/2006 | Shekunov et al. | 210/634 |
| 2006/0104916 A1 | 5/2006 | Shekunov et al. | 424/46 |
| 2006/0145375 A1 | 7/2006 | Chattopadhyay et al. | 264/13 |
| 2006/0258798 A1 | 11/2006 | Richard et al. | 524/544 |
| 2007/0267768 A1 | 11/2007 | Chattopadhyay et al. | 264/14 |

FOREIGN PATENT DOCUMENTS

| | | | |
|---|---|---|---|
| EP | 0 405 284 | | 1/1991 |
| EP | 0 464 163 | | 1/1992 |
| EP | 0 598 606 | | 5/1994 |
| EP | 0 683 804 | | 11/1995 |
| EP | 0 744 992 | | 12/1996 |
| EP | 784 506 | | 7/1997 |
| EP | 0 831 786 | | 4/1998 |
| EP | 0857114 B1 * | | 9/2000 ... B41M 5/00 |
| EP | 1 549 410 | | 7/2005 |
| EP | 1 551 523 | | 7/2005 |
| EP | 1 588 700 | | 10/2005 |
| JP | 11-255925 | | 9/1999 |
| WO | WO 90/09780 | | 9/1990 |
| WO | WO 91/09079 | | 6/1991 |
| WO | WO 94/09913 | | 5/1994 |
| WO | WO 94/18264 | | 8/1994 |
| WO | WO 95/21688 | | 8/1995 |
| WO | WO 95/24830 | | 9/1995 |
| WO | WO 96/40072 | | 12/1996 |
| WO | WO 98/07054 | | 2/1998 |
| WO | WO 98/15348 | | 4/1998 |
| WO | WO 98/51347 | | 11/1998 |
| WO | WO 99/19085 | | 4/1999 |
| WO | WO 99/25322 | | 5/1999 |
| WO | WO 00/72830 | | 12/2000 |
| WO | WO 00/76483 | | 12/2000 |
| WO | WO 01/15664 | | 3/2001 |
| WO | WO 01/37808 | | 5/2001 |
| WO | WO 01/68054 | | 9/2001 |
| WO | WO 01/89481 | | 11/2001 |
| WO | WO 01/91729 | | 12/2001 |
| WO | WO 02/47893 | | 6/2002 |
| WO | WO 02/090085 | | 11/2002 |
| WO | WO 03/013478 | | 2/2003 |
| WO | WO 03/074028 | | 9/2003 |
| WO | WO 03/078508 | | 9/2003 |
| WO | WO 2004/024802 | | 3/2004 |
| WO | WO 2004/043437 | | 5/2004 |
| WO | WO 2004/071634 | | 8/2004 |
| WO | WO 2005/004838 | | 1/2005 |
| WO | WO 2005/035088 | | 4/2005 |
| WO | WO 2005/042219 | | 5/2005 |
| WO | WO 2005/042623 | | 5/2005 |
| WO | WO 2005/073285 | | 8/2005 |
| WO | WO 2005/079752 | | 9/2005 |
| WO | WO 2006/093390 | | 9/2006 |
| WO | WO 2007/090870 | | 8/2007 |
| WO | WO 2008/045516 | | 4/2008 |
| WO | WO 2010/004287 | | 1/2010 |
| WO | WO 2010/004299 | | 1/2010 |

OTHER PUBLICATIONS

Definition of derivative, from http://cancerweb.ncl.ac.uk/cgi-bin/omd?query=derivative, pp. 1-5, accessed Jul. 7, 2005.*

Definition of precursor, from http://medical-dictionary.thefreedictionary.com/p/precursor, pp. 1-2, accessed May 23, 2014.*

Hydroxypropyl methyl cellulose, from http://www.chemicalbook.com/ChemicalProductProperty_EN_CB3225318.htm, pp. 1-2, accessed May 22, 2014.*

Vehring, Pharmaceutical Particle Engineering via Spray Drying, Pharmaceutical Research, 2008, 25, pp. 999-1022.*

Higuchi, Mechanism of Sustained-Action Medication Theoretical Analysis of Rate of Release of Solid Drugs Dispersed in Solid Matrices, Journal of Pharmaceutical Sciences, 1963, 52, pp. 1145-1149.*

Muller, Prodrug Approaches for Enhancing the Bioavailability of Drugs eith Low Solubility, Chemistry & Biodiversity, 2009, 6, pp. 2071-2083.*

"Liquid State Activation", Biorise Technology Platform, accessed Mar. 22, 2007.

Abdallah et al., "Corrosion inhibition of nickel in sulphuric acid using tween surfactants," *Portugaliae Electrochimica Acta*, pp. 315-326, 2003.

Almeida et al., "Novozym 435 activity in compressed gases. Water activity and temperature effects," *Enzyme and Microbial Technology*, 22(6), 494-499, 1998.

Barbaras et al., "Crospovidone" in: *Analytical Profiles of Drug Substances and Excipients*, Brittain ed., San Diego: Academic Press Inc., pp. 95-97 (1996).

Yao et al., "Formation of microparticulate protein powders using a supercritical fluid antisolvent," *Biotechnol. Bioeng.*, 41:341-346, 1993.

Birkin et al., "Synthesis and application of new CO2-soluble vinyl pivalate hydrocarbon stabilisers via RAFT polymerisation," *Polym. Chem.*, 2:1293-1299, 2011.

Broadhead et al., "The spray drying of pharmaceuticals," *Drug Dev. Ind. Pharm.*, pp. 1169-1206, 1992.

Carli et al., "Influence of polymer characteristics on drug loading into crospovidone," *Int. J. Pharm.*, 33:115-124, 1986.

Carstensen, J. T., "Powder dosage forms, densities and blending," In: *Pharmaceutical Principles of Solid Dosage Forms*, Lancaster, pp. 15-32, 1993.

Castellanos, "The relationship between attractive interparticle forces and bulk behaviour in dry and uncharged fine powders," *Adv. Phys.*, 54(4), 263-376, 2005. (abstract), Abstract only.

Cleland et al., "Recombinant human growth hormone poly(lactic-co-glycolic acid) (PLGA) microspheres provide a long lasting effect," *J. Controlled Release*, pp. 193-205, 1997.

Cleland et al., "Stable formulations of recombinant human growth hormone and interferon-y for microencapsulation in biodegradable microspheres," *Pharm. Res.*, pp. 1464-1475, 1996.

Conway, S. E. et al., "Poly(lactide-co-glycolide) solution behaviour in supercritical CO2, CHF3 and CHClF2," *J. Appl. Polym. Sci.*, (80):1155-1161, 2001.

Cook, D. M. et al., "The pharmacokinetic and pharmacodynamic characteristics of a long-acting growth hormone (GH) preparation (nutropin depot) in GH-deficient adults," *J. Clin. Endocrinol. Metab.*, 87(10):4508-4514, 2002.

Cooper A.I., "Porous materials and supercritical fluids," *Adv. Mater.*, 15(13), 1049-1059, 2003.

Davies et al., "Supercritical fluid encapsulation of human growth hormone maintains protein integrity during processing and release," *BPC Science*, abstract only (2006), Abstract only.

Yang et al., "Human osteoprogenitor bone formation using encapsulated bone morphogenetic protein 2 in porous polymer scaffolds," *Tissue Engineering*, 10(7/8):1037-1045, 2004.

Domb, A. J. et al., "Chapter 8: Polyanhydrides" in: *Handbook of Biodegradable Polymers*, Harwood Academic Publishers, 1997.

Duarte et al., "Supercritical fluids in biomedical and tissue engineering applications: a review," *Int. Mater. Rev.*, (54)4: 214-222, 2009.

(56) References Cited

OTHER PUBLICATIONS

Dumitriu, *Polymeric Biomaterials*, Marcel Dekker, Inc.,1994, Front page and publish information only.
Ed. Joseph C. Salamone, *Concise Polymeric Materials: Encyclopaedia*, CRC Press, 1999.
Fontes et al., "Cutinase activity and enantioselectivity in supercritical fluids," *Ind. Eng. Chem. Res.*, 37 :3189-3194, 1998.
Wei et al., "Stabilization of recombinant human growth hormone against emulsification-induced aggregation by Pluronic surfactants during microencapsulation," *International Journal of Pharmaceutics*, 338:125-132, 2007.
Griffin, W. C., "Calculation of HLB values of non-ionic surfactants," *J. Soc. Cosmet. Chem.*, 5:249-256, 1954.
Hao et al., "Supercritical fluid assisted melting of poly(ethylene glycol): a new solvent-free route to microparticles," *J. Mater. Chem.*, 15 :1148-1153, 2005.
Hao et al., "Plasticization and spraying of poly(DL-lactic acid) using supercritical carbon dioxide:control of particle size," *J. Pharmaceutical Sciences*, 93(4) :1083-1090, 2004.
Heller, "Use of poly(ortho esters) and polyanhydrides in the development of peptide and protein delivery systems," *ACS Symposium Series*, 567:292-305, 1994.
Davies et al., "Applications of supercritical CO2 in the fabrication of polymer systems for drug delivery and tissue engineering," *Adv. Drug Delivery Rev.*, 60:373-387, 2008.
Pini et al., "Sorption and swelling poly(D, L-lactic acid) and poly(lactic-co-glycolic acid) in supercritical CO2," *Macromol. Symp.*, 259:197-202, 2007.
Lee et al., "Successful dispersion polymerization in supercritical CO2 using polyvinylalkylate hydrocarbon surfactants synthesized and anchored via RAFT," *J. Am. Chem. Soc.*, 130: 12242-12243, 2008.
Howdle et al., "Supercritical fluid mixing: preparation of thermally sensitive polymer composites containing bioactive materials," *Chem. Commun.*, pp. 109-110, 2001.
James et al., "Pseudo-poly(amino acid)s: examples for synthetic materials derived from natural metabolites," in: *Controlled Drug Delivery Challenges and Strategies*, pp. 389-403, 1993.
Johnson et al., "The stabilization and encapsulation of human growth hormone into biodegradable microspheres," *Pharm. Res.*, 14(6):730-735, 1997.
Jung, J. et al., "Particle design using supercritical fluids: literature and patent survey," *Journal of Supercritical Fluids*, 20:179-219, 2001.
Kazarian et al., "Partitioning of solutes and cosolvents between supercritical CO2 and polymer phases," *J. Supercritical Fluids*, 13:107-112, 1998.
Kibbe, Ed. et al., *Handbook of Pharmaceutical Excipients*, $3^{rd}$ Ed., Pharmaceutical Press, 2000, Front page only.
Kim et al., "Biodegradable polymeric microspheres with 'open/closed' pores for sustained release of human growth hormone," *J. Controlled Release*, 112:167-174, 2006.
Kim et al., "Microencapsulation of naproxen using rapid expansion of supercritical solutions," *Biotechnol. Prog.*, 12:650-661, 1996.
Krause et al., "Porous monofilaments by continuous solid-state foaming," *Ing. Eng. Chem. Res.*, 41:1195-1204, 2002.
Lipincott Ed. et al., "Chapter 37: Powders," In: *Remington: The Science and Practice of Pharmacy*, pp. 681-699, 2000.
Lloyd et al., "Azopolymers: a means of colon specific drug delivery?" *Int. J. Pharm.*, 106:255-260, 1994.
Maa et al., "Spray-drying of air-liquid interface sensitive recombinant human growth hormone," *J. Pharm. Sci.*, 87(2):152-158, 1998.
Mori et al, "Reversible control onenzymatic transglycosylations in supercritical fluoroform using a lipid-coated β-D-Galactosidase," *JACS*, 124(7) :188-1 189, 2002.
Niehaus, M. et al., "Coating of particles in a fluidized bed using supercritical carbon dioxide," *Proceedings of Meeting in Supercritical Fluids*, pp. 361-367, 1998.
Park and Suh, "Filamentary extrusion of microcellular polymers using a rapid decompressive element," *Polymer Engineering and Science*, 36(1):34-48, 1996.
Park et al., "Low density microcellular foam processing in extrusion using CO2," *Polymer Engineering and Science*, 38(11): 1812-1823, 1998.
Pyo et al., "Size prediction of recombinant human growth hormone nanoparticles produced by supercritical fluid precipitation," *Anal. Bioanal.Chem.*, (387):901-907, 2007.
Schacht et al., "Biomedical applications of degradable polyphosphazenes," *Biotechnol. Bioeng.*, 52: 102-108, 1996.
Shim et al., "Adjustable solute distribution between polymers and supercritical fluids," *AICHE Journal*, 35(7):1097-1106, 1989.
Shine, "Chapter 18: Polymers and Supercritical fluids" in: *Ed. James E. Mark, Physical Properties of Polymers Handbook*, 249-256 (passim), 1996.
Tamada et al., "The development of polyanhydrides for drug delivery applications," *J. Biomater. Sci., Polym. Ed.*, 3(4):315-353, 1992.
Tom and Debenedetti, "Formation of bioerodible polymeric microspheres and microparticles by rapid expansion of supercriticial solutions," *Biotechnol. Prog.*, 7:403-411, 1991.
Tracy et al., "Development and scale-up of a microsphere protein delivery system," *Biotechnol. Prog.*, 14:108-115, 1998.
Van Hooff et al., "In vitro and in vivo testing of a parenteral controlled release formulation of human growth hormone manufactured using CriticalMix™," *Proc. Int. Symp. Control. Rel. Bioact. Mater.* 35, 2008.
Vasile and Kulshreshtha, Ed, A. K. *Handbook of Polymer Blends and Composites Volume 3A*, Rapra Technology Limited, pp. 6-7, 2002.
Watson et al., "Incorporation of proteins into polymer materials by a novel supercritical fluid processing method," *Adv. Mater.*, 14(24): 1802-1804, 2002.
Whitaker et al., "The production of protein-loaded microparticles by supercritical fluid mixing and spraying," *J. Controlled Release*, 101:85-92, 2005.

\* cited by examiner

Example 1 – PLGA / BSA 10 wt %

Example 2 – PLGA / BSA 10 wt % / SOLUTOL® 10 wt %

Example 3 – PLGA / BSA 10 wt % / Kolidon 12.2 wt %

Example 1 – PLGA / BSA 10 wt %

Example 2 – PLGA / BSA 10 wt % / SOLUTOL® 10 wt %

Example 3 – PLGA / BSA 10 wt % / Kolidon 12.2 wt %

90% w/w RG502H / 10% BSA

87%w/w RG502H / 3%w/w SOLUTOL® HS15 / 10%w/w BSA

PROCESS FOR PREPARING MICROPARTICLES

CROSS-REFERENCE TO RELATED APPLICATIONS

This application is a national phase application under 35 U.S.C. §371 of International Patent Application No. PCT/GB2009/001711 filed Jul. 10, 2009 which claims priority to Great Britain Patent Application No. 0812742.5 filed Jul. 11, 2008. The entire text of the above-referenced disclosures are specifically incorporated herein by reference without disclaimer.

STATEMENT REGARDING FEDERALLY SPONSORED RESEARCH OR DEVELOPMENT

Not Applicable

BACKGROUND OF THE INVENTION

1. Field of the Invention

The present invention relates to a process for preparing a composition comprising a biologically active material. More particularly, the invention relates to a process for producing microparticles comprising a biologically active material and a polymer. The microparticles produced using the process of the present invention can be used to deliver the biologically active material to a human or animal.

2. Description of Related Art

The process of the invention uses a supercritical fluid in the preparation of the microparticles and is particularly suitable for producing microparticles comprising temperature-labile or solvent-labile biologically active materials.

Methods for the production of compositions comprising a biologically active material and a polymer using a supercritical fluid have been reported in the past.

U.S. Pat. No. 5,340,614, WO91/09079 and U.S. Pat. No. 4,598,006 describe methods for providing bioactive material in a biodegradable polymer using supercritical fluids (SCF) to confer porosity during processing of the polymer.

U.S. Pat. No. 5,340,614 describes a method comprising dissolution of additive in a carrier solvent (liquid e.g. water or ethanol). A supercritical fluid (SCF) is then used to allow penetration of the carrier liquid/additive solution into the polymer.

WO91/09079 describes the use of SCF to introduce porosity into biodegradable polymers. If a bioactive material is present, a carrier solvent is required to dissolve the bioactive and to impregnate.

U.S. Pat. No. 4,598,006 describes a method for impregnating a thermoplastic polymer with an impregnation material in a volatile swelling agent at or near supercritical conditions, swelling the polymer and reducing the conditions so that the swelling agent diffuses out.

WO 98/51347 describes a method for the encapsulation of a biologically active material within a biodegradable polymer matrix, without the use of solvents or high temperatures. A supercritical fluid is used to depress the melting or glass transition temperature of the polymer so that the biologically active material can be mixed with the polymer at low temperatures and in the absence of organic or aqueous solvents. This document does not describe ways of optimising the processing of the materials.

WO03/013478 also describes a method of encapsulating an active substance in an interpolymer complex using supercritical fluids. Methods are described involving the dissolution of an interpolymer complex, or components thereof, in a supercritical fluid, or the dissolution of a supercritical fluid in an interpolymer complex. In both these systems an active substance is then encapsulated.

The listing or discussion of an apparently prior-published document in this specification should not necessarily be taken as an acknowledgement that the document is part of the state of the art or is common general knowledge.

The process of the prior art can be associated with problems such as low yield. By this we mean that use of the prior art processes can result in a lower than desirable level of recovery of a product comprising the biologically active material. This can result in a high level of wastage of often expensive biologically active materials.

The solid products of the processes of the prior art often have an irregular shape and/or size and/or an undesirably high surface area. This can make recovery of the product, often resulting in low yields and the use and/or the further processing of the product difficult.

BRIEF SUMMARY OF THE INVENTION

It is an object of the present invention to provide a process that addresses one or more of these problems and/or other drawbacks that may be associated with the processes of the prior art.

It has surprisingly been found that the use of certain processing aids in a process for the incorporation of a biologically active material into a polymer using a supercritical fluid can addresses one or more of these problems.

The present invention provides a process for preparing microparticles comprising a biologically active material and a polymer and having a mean particle size expressed as the volume mean diameter (VMD) of from 10 to 500 µm, wherein the biologically active material is substantially insoluble in the polymer, which process comprises:
 a. contacting a mixture of the biologically active material or a precursor thereof, the polymer or a precursor thereof and a processing aid with a supercritical fluid which is capable of swelling the polymer under temperature and pressure conditions necessary to maintain the fluid in a supercritical state;
 b. allowing the supercritical fluid to penetrate and liquefy the polymer, whilst maintaining the temperature and pressure conditions so that the fluid is maintained in a supercritical state;
 c. releasing the pressure to precipitate microparticles comprising the biologically active agent and the polymer.

BRIEF DESCRIPTION OF THE DRAWINGS

FIG. 1—SEM images of particles produced in the absence of processing aid (upper), using SOLUTOL® HS15 as the processing aid (middle) and using Kolidon as the processing aid (lower). All images are taken at ×90 magnification.

FIG. 3 shows: SEM images of representative particles produced in Example 3.

DETAILED DESCRIPTION OF THE INVENTION

Figure 1:
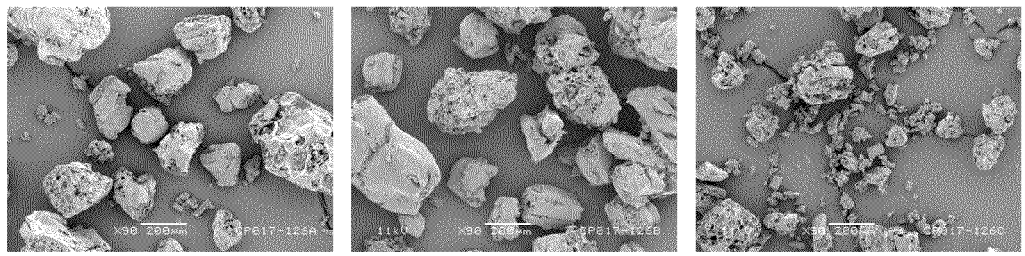
FIG. 1 shows.
Figure 1:
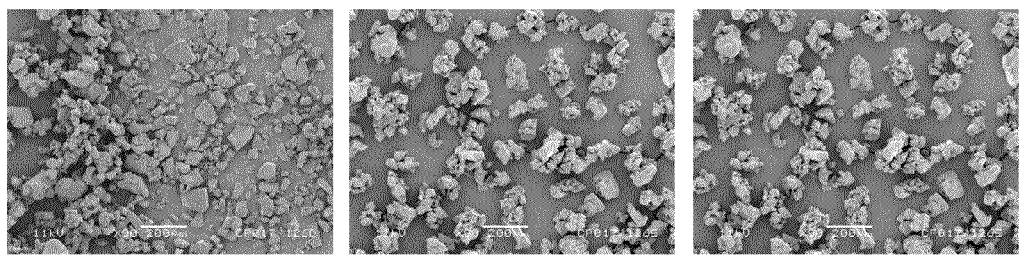
Figure 1:
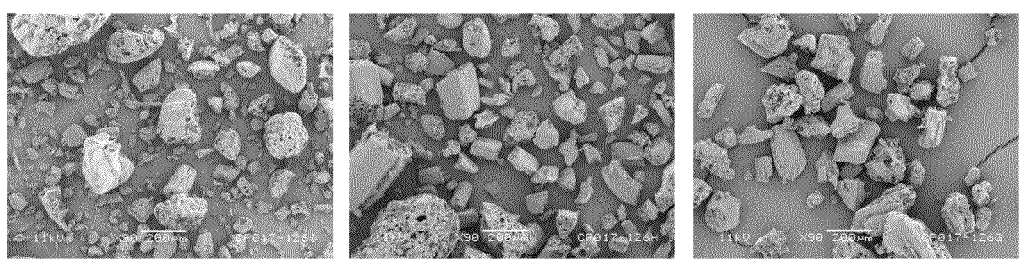
Figure 2:
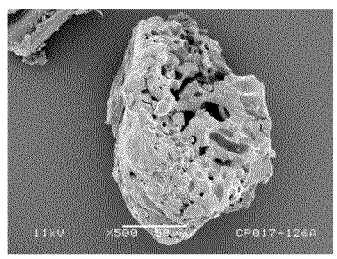
FIG. 2 shows: SEM images of representative particles produced in the absence of processing aid (upper), using SOLUTOL® HS15 as the processing aid (middle) and using Kolidon as the processing aid (lower).
Figure 2:
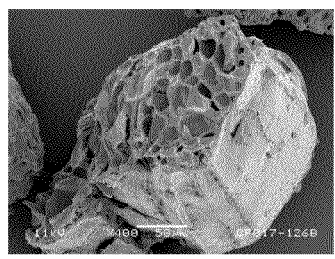
Figure 2:
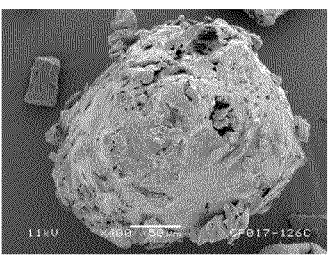
Figure 2:
Figure 2:
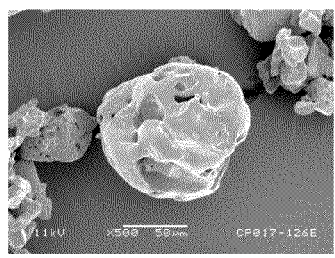
Figure 2:
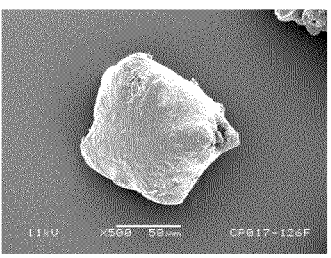
Figure 2:
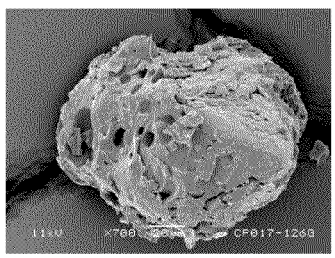
Figure 2:
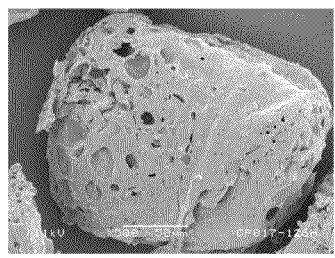
Figure 2:
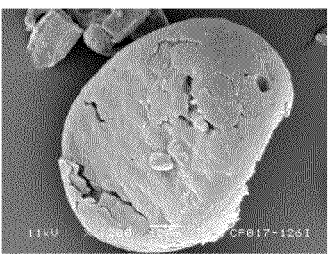
Figure 3A:
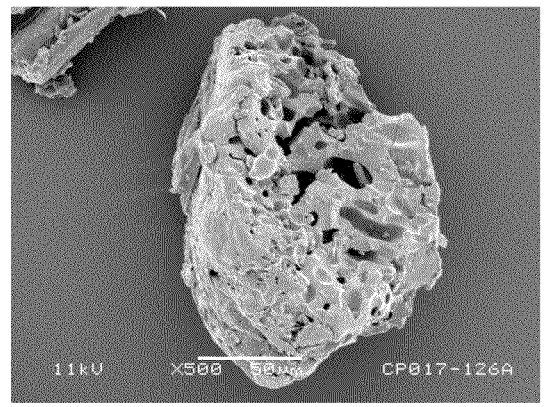
FIG. 3(A) shows SEM images of representative particles comprising 90% w/w RG502H 10% w/w BSA produced in Example 3.
Figure 3B:
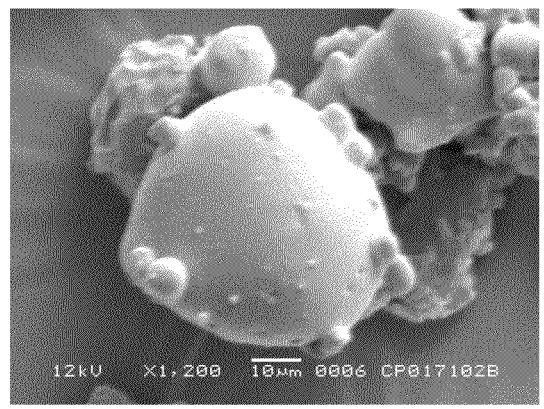
FIG. 3(B) shows SEM images of representative particles comprising 87% w/w RG502H 3% w/w SOLUTOL® HS15 10% w/w BSA produced in Example 3.

When a biologically active material (rather than a precursor thereof) is used, the microparticles produced comprise the biologically active material in substantially unchanged chemical form, and optionally in substantially unchanged physical form.

The process is preferably carried out substantially in the absence of additional carriers or solvents. More preferably, the process is carried out in the absence of additional carriers or solvents.

Without wishing to be bound by theory, it is believed that the absence of additional carriers and solvents helps to ensure that the biologically active material is substantially unchanged in chemical form and preferably also in physical form during the process of the invention. This means that the biologically active material retains its activity/performance.

In step b of the process of the invention the polymer swells. This means that the supercritical fluid dissolves in or permeates the polymer, leading to a depression of the polymer's melting point. This depressions of the polymer's melting point allows it to liquefy (ie become fluid without dissolving) at a temperature below its melting point. Thus, it is important that the polymer and the supercritical fluid are selected so that the fluid swells but does not dissolve the polymer. References such as Shine, Chapter 18: Polymers and Supercritical Fluids in Physical Properties of polymers Handbook, 249-256 (passim) (James E Mark ed. 1993), which is incorporated herein by reference, can be used to determine suitable combinations of polymer and supercritical fluid.

In step b the mixture may be blended or mixed, although this is not essential. This may be achieved using methods well known in the art, for example by agitation with associated shear thinning, for example with aeration or fluidizing gas flow, stirring or the like, more preferably according to the process of U.S. Pat. No. 5,548,004 (Ferro Corp) the contents of which are incorporated herein by reference.

Step b is typically carried out over a time period of from 1 minute to several hours, for example from 5 minutes to 3 hours, time periods of from about 30 minutes to 2 hours, for example about 1 hour are preferred.

The ingredients used in the present invention may be combined in any desired order, prior to, or during application of supercritical conditions. For example, prior to step a the polymer and the biologically active material and optionally the processing aid may be mixed. As a particular, non-limiting example, the biologically active material may be mixed with the polymer using a freeze drying technique. Using this method can produce a mixture of the biologically active material and the polymer in which the biologically active material is distributed on the surface of the polymer.

The process of the invention may be carried out as a batch-wise or as a continuous process.

Step c may be carried out using any suitable method known in the art. For example in situ, by depressurizing a pressure vessel in which the process is carried out, and simultaneously or otherwise ceasing mixing. Alternatively, the contents of pressure vessel in which the process is conducted may be discharged into a second pressure vessel at lower pressure whereby a homogeneous porous powder of polymer as hereinbefore defined is obtained by known means. Methods which comprise spraying into liquid nitrogen can also be used Step c can be carried out using techniques for removing a gas, which are similar to spray drying techniques. Apparatus suitable for these techniques and the techniques themselves, are well known.

Step c can be used to facilitate control of the size of the microparticles. Typically the blended mixture is removed from the mixing chamber (which is under supercritical conditions) into a separate container (which is not under supercritical conditions and may for example be under atmospheric conditions) through a nozzle or like orifice. The size of the aperture of the nozzle or orifice can optionally be controlled to control the size of the microparticles. Altering the conditions under which the blended material is removed from the supercritical fluid or the rate of removal can also affect that particle size.

In step c, the pressure can be released over a time period of fractions of a second to several days. It is currently preferred to release the pressure rapidly. By rapidly we mean over a period of 5 minutes or less, more preferably 1 minute or less, more preferably a second or less, for example half a second or less.

The polymer used in the present invention may be a single polymer or a mixture of two or more polymers. For example, two, three, four or more polymers may be used. Herein the reference to "the polymer" or "a polymer" is intended to encompass the plural unless the context indicates otherwise.

Any polymer that is subject to swelling by a supercritical fluid and which is suitable for introduction into or association with the human or animal body or living matter in non-toxic manner may be used in the process of the invention. Suitable polymer materials include synthetic biodegradable polymers such as those disclosed in "Polymeric Biomaterials" ed. Severian Dumitriu, ISBN 0-8247-8969-5, Publ. Marcel Dekker, New York, USA, 1994 (incorporated herein by reference), synthetic non-biodegradable polymers; and natural polymers. The polymer may be selected from homopolymers, block and random copolymers, polymeric blends and composites of monomers which may be straight chain, (hyper) branched or cross-linked.

Non-limiting examples of polymers which may be used in the process of the invention include those listed below.

Synthetic biodegradable polymers such as polyesters including poly(lactic acid) (PLA), poly(glycolic acid) (PGA), copolymers of lactic and glycolic acid (PLGA), copolymers of lactic and glycolic acid with poly(ethyleneglycol), poly(e-caprolactone) (PCL), poly(3-hydroxybutyrate) (PHB), poly (p-dioxanone), poly(propylene fumarate); modified polyesters such as poly(ether ester) multiblock copolymers such as those based on poly(ethylene glycol) and poly(butylenes terephthalate); poly(ortho esters) including Polyol/diketene acetals addition polymers as described by Heller in: ACS Symposium Series 567, 292-305, 1994 (incorporated herein by reference); Polyanhydrides including poly(sebacic anhydride) (PSA), poly(carboxybiscarboxy phenoxyphenoxyhexane) (PCPP), poly[bis(p-carboxyphenoxy)methane] (PCPM), copolymers of SA, CPP and CPM, as described by Tamada and Langer in Journal of Biomaterials Science-Polymer Edition, 3, 315-353, 1992 and by Domb in Chapter 8 of the Handbook of Biodegradable Polymers, ed. Domb A. J. and Wiseman R. M., Harwood Academic Publishers (both of which are incorporated herein by reference); Poly(amino acids); Poly(pseudo amino acids) including those described by James and Kohn in pages 389-403 of Controlled Drug Delivery Challenges and Strategies, American Chemical Society, Washington DC. (incorporated herein by reference); Polyphosphazenes including derivatives of poly[(dichloro) phosphazene], poly[(organo)phosphazenes], polymers described by Schacht in Biotechnology and Bioengineering, 52, 102-108, 1996 (incorporated herein by reference); and Azo polymers including those described by Lloyd in International Journal of Pharmaceutics, 106, 255-260, 1994 (incorporated herein by reference).

Synthetic non-biodegradable polymers such as vinyl polymers including polyethylene, poly(ethylene-co-vinyl acetate), polypropylene, poly(vinyl chloride), poly(vinyl acetate), poly(vinyl alcohol) and copolymers of vinyl alcohol and vinyl acetate, poly(acrylic acid) poly(methacrylic acid), polyacrylamides, polymethacrylamides, polyacrylates, poly(ethylene glycol), poly(dimethyl siloxane), polyurethanes, polycarbonates, polystyrene and derivatives.

Natural polymers such as carbohydrates, polypeptides and proteins including starch, cellulose and derivatives including ethylcellulose, methylcellulose, ethylhydroxy-ethylcellulose, sodium carboxymethylcellulose; Collagen; Gelatin; Dextran and derivatives; Alginates; Chitin; and Chitosan.

A mixture of one or more of the polymers set out above may be used as the polymer component. For the avoidance of doubt a mixture of one or more classes of polymers may be used (e.g. a polyester and a polyanhydride) and/or one or more particular polymers in a class.

Preferred polymers include non-biodegradable polymers such as ester urethanes or epoxy, bis-maleimides, methacrylates such as methyl or glycidyl methacrylate, tri-methylene carbonate, di-methylene tri-methylene carbonate; biodegradable synthetic polymers such as poly(glycolic acid), polyglycolide, poly(lactic acid), polylactide, poly(p-dioxanone), polydioxepanone, poly(alkylene oxalates), modified polyesters such as poly(ether ester) multiblock copolymers such as those based on poly(ethylene glycol) and poly(butylenes terephthalate); and poly(caprolactones) such as poly(gamma-caprolactone).

In a further embodiment, the polymer component comprises PCL, PHB, poly(ether ester) multiblock copolymers, PLGA, PLA, or a combination thereof, for example PLGA, PLA, or a combination of PLA and PLGA.

PLGA is poly(lactic-co-glycolic acid). The amount of lactic acid and glycolic acid comonomers present in the PLGA which may be used may vary over a wide range. The PLGA may have a molar ratio of lactic acid:glycolic acid of from about 90:10 to about 10:90, such as from about 75:25 to about 25:75, for example about 50:50.

The molecular weight of a polymer is related to its inherent viscosity. The inherent viscosity of the polymers that may be used in the process of the invention (e.g. PLGA and PLA) typically is from about 0.1 to about 1.5 dl/g, such as from about 0.11 to about 1 or about 0.12 to about 0.5, for example from about 0.15 to about 0.30 or about 0.16 to about 0.24.

In one aspect of the invention, the biodegradable polymer component comprises both PLGA and PLA. The ratio (by weight) of PLGA:PLA when they are both present in the biodegradable polymer component typically is from about 95:5 to about 5:95. Preferably, there is about the same or more PLGA present than PLA, for example the weight ratio of PLGA:PLA is from about 90:10 to about 40:60, such as from about 85:15 to about 50:50, for example from about 75:25 to about 60:40.

Typically, a polymer or combination of polymers which is inert to the biologically active substance to be used will be used.

The polymer is typically used in an amount of from about 5 to about 98% by weight of the total weight of the polymer, the biologically active material and the processing aid, such as from about 25 to about 96.5%, or from about 45 to about 93% or from about 60 to about 85%.

Without being bound by theory, it is believed that the polymer component may help to reduce the "burst release" of the composition produced by the process of the invention when it is injected into the body. By "burst release", we mean the amount of somatotrophic hormone, as a percentage of the total amount of biologically active material in the composition, that is released immediately or substantially immediately (e.g. within about 1 hour) following administration in vivo or dissolution in vitro using standard dissolution tests (e.g. as described in the European pharmacopoeia, which is incorporated herein by reference).

Typically, the burst release of the compositions made by the process of the invention is less than about 80%, preferably, less than 70, 60, 50, 40, 30, 20 or 10%.

It is also believed that the polymer component helps to control/sustain/delay the release of the biologically active material following "burst". In fact, it is thought that the release of biologically active material following burst in some cases may be too slow using a polymer alone. It is believed that the processing aid in the compositions made by the process of the invention helps to increase the rate of release of the protein following burst.

Processing aids which are suitable for use in the process of the present invention include oligomers or polymers of fatty acids, fatty acid esters, hydroxy fatty acid esters, pyrolidones or polyethers, medium and long chain triglycerides, poloxamers, phospholipids, derivatives thereof and mixtures thereof.

Fatty acids which are suitable for use as processing aids include linear and cyclic (preferably linear), saturated and unsaturated fatty acids comprising from 6 to 40, preferably from 9 to 30 and most preferably from 11 to 18 carbon atoms. The saturated fatty acids have the general formula $C_nH_{2n}O_2$, wherein n is from 7 to 40, preferably from 9 to 30 and most preferably from 11 to 18. The unsaturated fatty acids may have the formula $C_nH_{2n-2}O_2$, or $C_nH_{2n-4}O_2$ or $C_nH_{2n-6}O_2$ wherein n is from 7 to 40, preferably from 9 to 30 and most preferably from 11 to 18. Unsaturated fatty acids with 4 or more double bonds may also be used. Optionally, the fatty acids may be hydroxylated (e.g. 12-hydroxy steric acid). The hydroxy group(s) may be further esterified with another fatty acid (i.e. fatty acid oligomers or polymers). Unsaturated fatty acids may be in the cis- or trans-configurations or mixtures of both configurations may be used.

Examples of preferred fatty acids include stearic acid, oleic acid, myristic acid, caprylic acid and capric acid. Oils containing these and any of the foregoing fatty acids may also be used as the processing aid, e.g. cotton seed oil, sesame oil and olive oil.

Suitable fatty acid derivatives (e.g. esters) include those that can be derived from the fatty acids and hydroxyl fatty acids defined above. Preferred fatty acid esters are mono-esters and di-esters of fatty acids, and derivatives thereof, such as polyethylene glycol (PEG) mono-esters and di-esters of fatty acids. Suitable PEG's include those having from 2 to 200 monomer units, preferably 4 to 100 monomer units, for example 10 to 15 monomer units. Examples include PEG stearate and PEG distearate, each available with varying PEG chain lengths e.g. polyoxyl 40 stearate (Crodet S40, Croda) and PEG-8 distearate (Lipopeg 4-DS, Adina).

A particularly preferred fatty acid ester for use in the process of the invention is SOLUTOL® HS 15, which is available from BASF. SOLUTOL® consists of polyglycol mono- and di-esters of 12-hydroxystearic acid and of about 30% free polyethylene glycol and is an amphiphilic material having a hydrophilic-lipophilic balance of from about 14 to about 16.

Further examples of fatty acid derivatives include fatty acids esterified with polyoxyethylene sorbitan compounds, such as the "Tween" compounds (e.g. polyoxyethylene (20)

sorbitan monooleate, also known as TWEEN® 80) and fatty acids esterified with sorbitan compounds, such as the "Span" compounds (e.g. sorbitan monooleate, also known as Span 80).

Suitable pyrolidones include 2-pyrolidone, such as Soluphor® (BASF) and N-methyl-2-pyrrolidone.

Suitable polyethers include those comprising monomers comprising from 2 to 10 carbon atoms, preferably polyethylene glycols (PEGs) and polypropylene glycols (PPG's).

Poloxamers are block copolymers of ethylene oxide and propylene oxide. They have the general formula $HO(C_2H_4O)_a(C_3H_6O)_b(C_2H_4O)_aH$ wherein a is typically from 2 to 130 and b is typically from 15 to 67. Several different types of poloxamer are available commercially, from suppliers such as BASF, and vary with respect to molecular weight and the proportions of ethylene oxide "a" units and propylene oxide "b" units. Poloxamers suitable for use in the subject invention typically have a molecular weight of from 2,500 to 18,000, for example from 7,000 to 15,000 Da. Particular examples of commercially available poloxamers include poloxamer 188, which structurally contains 80 "a" units and 27 "b" units, and has a molecular weight in the range 7680 to 9510 and poloxamer 407 which structurally contains 101 "a" units and 56 "b" units, and has a molecular weight in the range 9840 to 14600 (Handbook of Pharmaceutical Excipients, editor A. H. Kippe, third edition, Pharmaceutical Press, London, UK, 2000, which is incorporated herein by reference).

Suitable triglycerides include saturated and unsaturated medium and long chain mono-, di- and tri-glycerides.

Typically, medium chain mono-, di- and tri-glycerides have a formula $(CH_2OR_1)(CH_2OR_2)(CH_2OR_3)$ wherein $R_1$, $R_2$ and $R_3$ are independently H or $-C(O)(CH_2)_nCH_3$ (where n=6 to 8), provided that at not all $R_1$, $R_2$ and $R_3$=H. Preferable medium chain mono-, di- and tri-glycerides consist of a mixture of esters of saturated fatty acids mainly of capryilic acid and capric acid e.g. Crodamol GTC/C (Croda), Miglyol 810, Miglyol 812, Neobee M5.

Typically, long chain mono-, di- and tri-glycerides have a formula $(CH_2OR_1)(CH_2OR_2)(CH_2OR_3)$ wherein $R_1$, $R_2$ and $R_3$ are independently H or $-C(O)(CH_2)_mCH_3$ (where m=7 to 17), provided that at not all $R_1$, $R_2$ and $R_3$=H. A preferred long chain mono-, di- and tri-glyceride is Witepsol.

A particularly preferred processing aid that may be used in the present invention is SOLUTOL® HS 15 (available from BASF).

The preferred processing agents for use in the invention are amphiphilic. Suitable amphiphilic compounds typically have a hydrophilic-lipophilic balance (HLB) of from about 1 to about 50, preferably from about 5 to 30 and most preferably from about 12 to about 24. HLB values can be calculated using the method of Griffin published in Griffin W. C., 1954, Calculation of HLB values of non-ionic surfactants, J. Soc. Cosmet. Chem. 5, 249-256 and Griffin W. C., 1955, Calculation of HLB values of non-ionic surfactants, Am. Perf. Essent. Oil Rev., 26-29 (both of which are incorporated herein by reference).

Polyethylene glycol (PEG) cannot be used as the only processing aid in the process of the invention.

The processing aids listed above may be used alone or in combination.

The total amount of processing aid used in the process of the invention is typically from about 0.1% to about 99.9%, preferably from about 0.2% to about 30% and most preferably from about 0.5% to 5% of the total weight of the biologically active material, the polymer and the processing aid.

Without wishing to be bound by theory, it is believed that the processing aid may act as a "molecular lubricant", reducing the interaction between polymer chains and the volume between chains, increasing the flowability between chains. This is thought to have the effect of reducing effects such as aggregation of the polymer, which may allow better mixing of the biologically active material within the polymer and the production of smaller and/or more regularly sized microparticles.

It has surprisingly been found that by the use of one or more of these processing aids in the process of the invention one or more of the following can be achieved: an increase in yield, reduction in particle size, narrower particle distribution, more spherical particle morphology.

The nature of the biologically active material used in the process of the invention is not particularly limited. However, the biological active material should not be soluble in the supercritical fluid. The biologically active material may be soluble or insoluble in the polymer or the processing aid. The biologically active material may be a pharmaceutical or veterinary product, i.e. as any pharmacologically active compounds that alter physiological processes with the aim of treating, preventing, curing, mitigating or diagnosing a disease.

Examples of biologically active materials that can be used include low molecular weight drugs, peptides and proteins and antigens.

By the term "low molecular drug" we mean a drug with a molecular weight of less than about 1000 Da. Examples of such drugs include, but are not limited to, acitretin, albendazole, albuterol, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme QI0, cyclobenzaprine, cyclosporine, danazol, dantrolene, dexchlopheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, risperidone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, zolmitriptan, zolpidem, and zopiclone acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metroprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine; vinorelbine; vitamin B12; warfarin sodium; yellow fever vaccine; zalcitabine; zanamavir; zolandronate; zidovudine The peptides and proteins which may be used in the invention typically have a molecular weight of from about 1 to about 300 kDa, more preferably from about 1 to about 150 kDa, more preferably from about 1 to 100 kDa and most preferably from about 1 to about 50 kDa. Examples of peptides and proteins that may be used include, but are not limited to, insulin, growth hormones such as human growth hormone (hGH), glucagons, leuprolide, growth hormone, Parathyroid hormone, calcitonin, vascular endothelium growth factor, Erythropoietin, heparin, cyclosporine, oxytocin, tyrosine, enkephalin, tyrotropin releasing hormone, follicle stimulating hormone, leuteinising hormone, vasopressin, and vasopressin analogs, catalase, superoxide dismutase, interleukin-II, interferons, colony stimulating factor, tumour necrosis factor, melanocyte stimulating hormone, glucagon-like peptide-1, glucagon-like peptide-2, katacalcin, cholecystekinin-12, cholecystekinin-8, exendin, gonadoliberin-related peptide, insulin-like protein, leucine-enkephalin, methionine-enkephalin, leumorphin, neurophysin, copeptin, neuropeptide Y, neuropeptide AF, PACAP-related peptide, pancreatic hormone, peptide YY, urotensin, intestinal peptide, adrenocorticotropic peptide, epidermal growth factor, prolactin, luteinising hormone releasing hormone (LHRH), LHRH agonists, growth hormone releasing factor, somatostatin, gastrin, tetragastrin, pentagastrin, endorphins, angiotensins. Thyrotropin releasing hormone, tumour necrosis factor, granulocyte-colony stimulating factor, granulocyte-macrophage-colony stimulating factor, macrophage-colony stimulating factor, heparinase, vascular endothelial growth factor, enzymes, and glycoproteins.

Alternatively, the biologically active material may be an absorbent for poisons, toxins and the like and may be defined as any natural or synthetic products capable of immobilising by absorption, interaction, reaction or otherwise naturally occurring or artificially introduced poisons or toxins.

The biologically active material used in the present invention may be in any suitable form. For example, it may be in a form suited for the function to be performed, for example in solid, semi-solid such as thixotrope or gel form, semi-fluid or fluid such as paste of liquid form. While it is preferred that the biologically active material does not undergo physical change during the process of the invention it is possible that the biologically active material may undergo physical change during the process. In this case the biologically active material to be used in the process of the invention can be in any suitable form provided that any physical change during the process of the invention results in the biological material being in a form suitable for its intended purpose.

It is preferred that the biologically active material is in the form of a solid, for example as particles or a powder. The size of the solid particles will depend on factors such as the nature of the biologically active material and the intended use of the biologically active material. Typically the solid particles have a size of from about 1 nm to about 100 μm.

The biologically active material may be miscible or immiscible with the polymer and supercritical fluid but is insoluble in the supercritical fluid.

The amount of the biologically active material used in the process of the invention is not particularly limited and as the skilled person will appreciate the amount of active material will depend on a variety of factors including the nature of the active material, the intended use, the intended dosage form and the intended dosage regimen. Typically the biologically active material is at least about 0.01% by weight of the total amount of the polymer, the processing aid and the biologically active material, preferably at least about 0.1%, more preferably at least about 1%, more preferably at least about 5%. The amount of the biologically active material typically does not exceed about 95% by weight of the total amount of the polymer, the processing aid and the biologically active material and is preferably 50% or less, for example from about 1 to about 50% or from about 2 to about 40%, such as from about 5 to about 30% or from about 10 to about 20% by weight.

The supercritical fluid used in the invention can be any fluid which may be brought into a supercritical state. As is known in the art, such fluids may be subjected to conditions of temperature and pressure up to a critical point at which the equilibrium line between liquid and vapour regions disappears. Supercritical fluids are characterised by properties which are both gas like and liquid like. In particular, the fluid density and solubility properties resemble those of liquids, whilst the viscosity, surface tension and fluid diffusion rate in any medium resemble those of a gas, giving gas like penetration of the medium Supercritical fluids which may be used include carbon dioxide, di-nitrogen oxide, carbon disulphide, aliphatic $C_{2-10}$ hydrocarbons such as ethane, propane, butane, pentane, hexane, ethylene, and halogenated derivatives thereof such as for example carbon tetrafluoride or chloride and carbon monochloride trifluoride, and fluoroform or chloroform, $C_{6-10}$ aromatics such as benzene, toluene and xylene, $C_{1-3}$ alcohols such as methanol and ethanol, sulphur halides such as sulphur hexafluoride, ammonia, xenon, krypton and the like. Preferably the fluid is carbon dioxide alone or in combination with one or more of the fluids listed above.

Optionally, the supercritical fluid may comprise a co-solvent such as acetone or an alcohol.

Typically these fluids may be brought into supercritical conditions at a temperature of from about 0 to about 300° C. and a pressure of from about $7\times10^5$ $Nm^{-2}$ to about $1\times10^8$ $Nm^{-2}$, preferably from about $12\times10^5$ $Nm^{-2}$ to about $8\times10^7$ $Nm^{-2}$ (7-1000 bar, preferably 12-800 bar).

It will be appreciated that the choice of fluid will depend on a variety of factors including the nature of the biologically active material and the polymer. The nature of the polymer is particularly important in the selection of the supercritical fluid. The fluid must swell the polymer to a sufficient extent so that when the pressure on the mixture is released the fluid will occupy the overwhelming majority of the total volume of the mixture (typically greater than 90% of the total volume). In practical terms, this means that the fluid should have an appropriate combination of high density (ie much greater than the density at atmospheric temperature and pressure) and high solubility in the polymer.

The amount of supercritical fluid used in the process of the invention can vary within wide limits and may depend on factors such as the nature of the polymer and the nature of the reaction vessel.

As used herein, the term "supercritical fluid" should be understood to encompass near supercritical fluids. That is highly compressed fluids that are below the critical temperature point but exhibit many of the same properties as true supercritical fluids. Correspondingly, the term "supercritical state" is considered to encompass near-supercritical state.

Additional components which may be used in the process of the invention include, but are not limited to, initiators, accelerators, hardeners, stabilisers, antioxidants, adhesion promoters, fillers and the like may be incorporated within the polymer. Markers and tags and the like may be incorporated to trace or detect administration or consumption of the composition according to known techniques.

If it is desired to introduce an adhesion promoter into the polymer composition, the promoter may be used to impregnate or coat particles of biologically active material prior to introduction into the polymer composition, by means of simple mixing, spraying or other known coating techniques, in the presence or absence of a fluid as hereinbefore defined. Preferably coating is performed in conjunction with mixing with fluid as hereinbefore defined. For example, the adhesion promoter may be dissolved in fluid as hereinbefore defined and the solution contacted with the biologically active material particles as hereinbefore defined. Alternatively, the adhesion promoter may be introduced into the autoclave during the mixing and/or polymerisation step whereby it attaches to the biologically active material particles in desired manner.

The biologically active material may be treated prior to or during the incorporation into the polymer with any suitable materials adapted to enhance the performance or mechanical properties thereof. The biologically active material may, for example, be treated with components such as binders adapted to promote adhesion to the polymer, dispersants to increase dispersion throughout the polymer and prevent aggregate formation, to increase dispersion as a suspension throughout a supercritical fluid, activators to accelerate any biofunctional effect in situ and the like. Preferably a biologically active material comprising hydroxapatite may be treated with binding species such as silanes and the like to increase adhesion of particles to the polymer.

Preferred adhesion promoters are soluble in the fluid as hereinbefore defined. This means that any residual promoter that does not bind to the biologically active material or to the polymer is removed when the microparticles are removed from the supercritical fluid.

The morphology of the microparticles of the invention is not particularly limited. For example the biologically active material may be distributed throughout the polymer substrate resembling a (co-)continuous morphology. The transition from coated or encapsulated particles to distributed mixtures may be merely a gradation of order of magnitude, whereby the microparticles may effectively comprise a plurality of biologically active material particles independently coated with or encapsulated by a continuous phase of polymer. This is conveniently termed particulate morphology.

It is an important feature of the invention that microparticles of relatively uniform size are produced.

The microparticles produced using the process of the invention have a mean particle size expressed as the volume mean diameter (VMD) of from about 10 to about 500 µm, preferably from about 20 to about 200 or 250 µm, more preferably from about 30 to about 150 µm, even more preferably from about 40 to 100 µm, for example from about 50 to about 80 µm. The volume mean diameter of the microparticles can be measured by techniques well known in the art such as laser diffraction.

Typically no more than 10% of the microparticles have a diameter ($D_{10\%}$) less than the lower limit of each of the size ranges quoted above respectively and at least 90% of the particles have a diameter ($D_{90\%}$) that does not exceed the upper limit of each of the size ranges quoted above respectively.

As is illustrated in the Examples below, the use of a processing aid as described above in the process of the invention significantly increases the yield of microparticles. Thus, the present invention provides the use of a processing aid as described above to increase or enhance the yield of microparticles comprising a biologically active material and a polymer in a process as described above wherein the increase in yield is relative to the yield obtained using the same process in the absence of a processing aid. Typically the use of a processing aid as defined above can increase the yield by at least 20%, preferably at least 50%, more preferably at least 100% or at least 200%.

The microparticles obtained using the process of the invention polymer may be characterised by their morphology, which may be determined by analysis of a cross section thereof.

The microparticles produced by the process of the invention have a relatively smooth surface and a surface area that is typically lower than that of microparticles produced by supercritical fluid processes of the prior art.

An ideal average surface area (IASA) for the particles of the invention can be calculated on the basis of the volume mean diameter (VMD) using the following equation.

$$IASA=4(pi)r^2$$

Wherein r is the volume mean radius (ie half the VMD)

Of course, this calculation assumes that the microparticles are spheres. Ideally, the microparticles produced in the process of the invention will be spheres. However, it is unlikely that all of the microparticles produced will be spherical (although they may be substantially spherical). Additionally, although the surface of the microparticles produced by the process of the invention is typically smoother than that of particles produced by previously used methods, not all of the particles will have a perfectly smooth surface.

This means that $4(pi)r^2$ is the lowest possible surface area for the microparticles of the invention. The microparticles of the invention typically have a surface area which is from about $4(pi)r^2$ to about $10,000 \times 4(pi)r^2$, preferably from about $4(pi)r^2$ to about $1000 \times 4(pi)r^2$, more preferably from about $4(pi)r^2$ to about $100 \times 4(pi)r^2$, for example from about $4(pi)r^2$ to about $10 \times 4(pi)r^2$, wherein r is half the VMD.

Preferably, the compositions produced by the process of the invention are "true blends" as opposed to phase-separated blends. By "true blends" we include the meaning that the compositions are well blended in a single, solvent free step. Differential scanning calorimetry (DSC) can be used to determine whether a true blend or a phase separated blend is obtained. This is explained in more detail below.

The or each polymer present in the compositions produced by the process of the invention will have a glass transition temperature ($T_g$), a melting temperature ($T_m$) or both a $T_g$ and $T_m$. The or each component that makes up the processing aid will have a glass transition temperature ($T_g$) or a melting temperature ($T_m$) if it is a solid.

In a true-blended composition, the or each $T_g$ of the polymer component will tend to merge with the $T_g$ of the or each processing aid (to exhibit one $T_g$) as shown by DSC. In contrast, in a phase-separated blend typical of the prior art, the $T_g$ of the or each polymer component will tend to remain distinct from the or each $T_g$ of the processing aid as shown by DSC.

Reference Example 1

Processing in the Absence of a Processing Aid

PLGA ($M_w$ 11 kDa, measured in THF relative to PS standards, 2.0 g) was pre mixed with Bovine Serum Albumin (0.2 g, 10 w.t. %, from Sigma Aldrich) and this mixture was loaded into the supercritical fluid PGSS processing rig. The system was sealed and pressurised with $CO_2$. The temperature and pressure were raised to approximately 40° C. and 2000 psi rendering the $CO_2$ a supercritical fluid. Whilst maintaining these conditions the PLGA/BSA were stirred for 60 min. The mixture was then expanded into a collection vessel using a cyclone and collected yielding a course free flowing powder. Three replicate batches were prepared.

Example 1

Processing with SOLUTOL® HS15

PLGA ($M_w$ 11 kDa, measured in THF relative to PS standards, 2.0 g) was pre mixed with SOLUTOL® HS15 (0.2 g, 10.0 w.t. %, from BASF) and Bovine Serum Albumin (0.2 g, 10 w.t. %). This mixture was loaded in to the supercritical fluid PGSS processing rig. The system was sealed and pressurised with $CO_2$. The temperature and pressure were raised to approximately 40° C. and 2000 psi rendering the $CO_2$ a supercritical fluid. Whilst maintaining these conditions the PLGA/SOLUTOL® HS15/BSA were mixed for 60 min. The mixture was then expanded into a collection vessel using a cyclone and collected as a fine, free flowing white powder. Three replicate batches were prepared.

Example 2

Processing with Kolidon 12

PLGA ($M_w$ 11 kDa, measured in THF relative to PS standards, 2.00 g) was pre mixed with Kollidon 12 (0.03 g, 2 w.t. %, from BASF) and Bovine Serum Albumin (0.2 g, 10 w.t. %). This mixture was loaded in to the supercritical fluid PGSS processing rig. The system was sealed and pressurised with $CO_2$. The temperature and pressure were raised to approximately 40° C. and 2000 psi rendering the $CO_2$ a supercritical fluid. Whilst maintaining these conditions the PLGA/Kollidon 12/BSA were mixed for 60 min. The mixture was then expanded into a collection vessel using a cyclone and easily collected as a course free flowing white powder. Three replicate batches were prepared.

TABLE 1

Average batch yield and particle size data for three replicates of each of Reference Example 1, Example 1 and Example 2.

| Example | Polymer | BAM | Processing Aid | Increase in Yield % | VMD | d90 | d50 | d10 | |
|---|---|---|---|---|---|---|---|---|---|
| Ref 1 | PLGA 11 kDa | BSA 10 wt % | | — | 126 18 | 248 27 | 110 19 | 27 10 | Average Std dev |
| 1 | PLGA 11 kDa | BSA 10 wt % | Solutol 10% | 243 | 129 13 | 279 33 | 98 11 | 30 5 | Average Std dev |

TABLE 1-continued

Average batch yield and particle size data for three replicates of each of Reference Example 1, Example 1 and Example 2.

| Example | Polymer | BAM | Processing Aid | Increase in Yield % | VMD | d90 | d50 | d10 | |
|---|---|---|---|---|---|---|---|---|---|
| 2 | PLGA 11 kDa | BSA 10 wt % | Kolidon 12.2.% | 0 | 103 20 | 201 26 | 90 23 | 23 8 | Average Std dev |

Example 3

PLGA ($M_w$ 11 kDa, measured in THF relative to PS standards, 2.0 g) was pre mixed with SOLUTOL® HS15 (0.06 g, 3.0 w.t. %) and Bovine Serum Albumin (0.2 g, 10 w.t. %). This mixture was loaded in to the supercritical fluid PGSS processing rig. The system was sealed and pressurised with $CO_2$. The temperature and pressure were raised to approximately 40° C. and 2000 psi rendering the $CO_2$ a supercritical fluid. Whilst maintaining these conditions the PLGA/SOLUTOL® HS15/BSA were mixed for 60 min. The product was easily collected as a fine, free flowing white powder.

TABLE 2

SOLUTOL ® HS15 Reduces Particle Size and Improves Morphology

| Formulation | D10 (µm) | D50 (µm) | D90 (µm) | Vmd (µm) |
|---|---|---|---|---|
| A 90% w/w RG502H 10% BSA (mean ± 1SD) | 27 ± 18 | 110 ± 19 | 248 ± 27 | 126 ± 18 |
| B 87% w/w RG502H 3% w/w SOLUTOL ® HS15 10% w/w BSA | 11 | 42 | 145 | 63 |

Example 4

Processing with Span 80

PLGA (Mw 11 kDa, measured in THF relative to PS standards, 0.73 g) was premixed with Span 80 (0.53 g, 25 w.t. %, from Sigma) and Risperidone (0.84 g, 40 w.t. %). The mixture was loaded into the supercrital fluid PGSS processing rig. The system was sealed and pressurised with $CO_2$. The temperature and pressure were raised to approximately 40° C. and 2000 psi rendering the $CO_2$ a supercritical fluid. Whilst maintaining these conditions the PLGA/Span 80/Risperidone were mixed for 60 min. The mixture was then expanded into a collection vessel using a cyclone and collected as a free flowing white powder.

TABLE 3

Batch yield and particle size data for Example 4.

| Example | Polymer | Processing Aid Content (% w/w) | Risperidone Content (%) | Yield (%) | D10 | D50 | D90 | VMD | |
|---|---|---|---|---|---|---|---|---|---|
| 1 | PLGA 11 kDa | SPAN 80 25% | 40 | 44 | 37.12 | 102.3 | 304 | 138 | |
| Ref 1 | PLGA 11 kDA | 0 | 40 | 9 ± 2.9 | 27 ± 8.8 | 88 ± 22.1 | 258 ± 171.8 | 118 ± 54.1 | Average Std Dev (n = 6) |

The invention claimed is:

1. A process for preparing microparticles comprising a biologically active material and a polymer, wherein the microparticles have a mean particle size expressed as the volume mean diameter (VMD) of from 10 to 500 µm, wherein the biologically active material is insoluble in the polymer, and wherein the process comprises the following sequential steps:
   a) contacting a mixture of the biologically active material, the polymer, and a processing aid with supercritical carbon dioxide,
   wherein the processing aid is selected from the group consisting of:
      (i) fatty acids, sorbitan monooleate, polyoxyethylene (20) sorbitan monooleate, fatty acid esters consisting of polyglycol mono- and di-esters of 12-hydroxystearic acid and of about 30% free polyethylene glycol;
      (ii) 2-pyrrolidone, N-methyl-2-pyrrolidone, polymers of pyrrolidones;
      (iii) polypropylene glycol;
      (iv) medium chain mono-, di-, and tri-glycerides having a formula $(CH_2OR_1)(CH_2OR_2)(CH_2OR_3)$ wherein $R_1$, $R_2$, and $R_3$ are independently H or $-C(O)(CH_2)_nCH_3$, wherein n is an integer from 6 to 8, provided that not all $R_1$, $R_2$, and $R_3$ are H; and
      (v) poloxamers having a general formula $HO(C_2H_4O)_a(C_3H_6O)_b(C_2H_4O)_aH$, wherein a is an integer from 2 to 130 and b is an integer from 15 to 67;
   b) allowing the supercritical carbon dioxide to penetrate and liquefy the polymer, whilst maintaining the temperature and pressure conditions so that the carbon dioxide is maintained in a supercritical state, and blending or mixing the supercritical carbon dioxide and liquefied polymer in a mixing chamber to form a blended mixture;
   c) removing the blended mixture from the mixing chamber into a separate container that is not under supercritical conditions through a nozzle or orifice, thereby forming the microparticles.

2. The process according to claim 1, wherein the processing aid is amphiphilic and has a hydrophilic-lipophilic balance of from about 1 to about 50.

3. The process according to claim 1, wherein the processing aid is selected from the group consisting of sorbitan monooleate, polyoxyethylene (20) sorbitan monooleate, and fatty acid esters consisting of polyglycol mono- and di-esters of 12-hydroxystearic acid and of about 30% free polyethylene glycol.

4. The process according to claim 3, wherein the processing aid is a fatty acid ester consisting of polyglycol mono- and di-esters of 12-hydroxystearic acid and of about 30% free polyethylene glycol.

5. The process according to claim 1, wherein the microparticles formed in step c) have a VMD of from about 40 to about 100 μm.

6. The process according to claim 5, wherein no more than 10% of the microparticles formed in step c) have a diameter ($D_{10\%}$) less than 40 μm and at least 90% of the particles have a diameter ($D_{90\%}$) of 100 μm or less.

7. The process according to claim 1, wherein the microparticles formed in step c) have a mean surface area which is from about $4(pi)r^2$ to about $10,000 \times 4(pi)r^2$, wherein r is half of the VMD.

8. The process according to claim 7, wherein the microparticles formed in step c) have a mean surface area which is from about $4(pi)r^2$ to about $1000 \times 4(pi)r^2$, wherein r is half of the VMD.

9. The process according to claim 7, wherein the microparticles formed in step c) have a mean surface area which is from about $4(pi)r^2$ to about $10 \times 4(pi)r^2$, wherein r is half of the VMD.

10. The process according to claim 1, wherein the amount of the processing aid is from 0.2 to 30% by weight of the total weight of the biologically active material, the polymer and the processing aid.

\* \* \* \* \*